United States Patent
Yu et al.

(10) Patent No.: US 7,122,201 B2
(45) Date of Patent: Oct. 17, 2006

(54) COMPOSITION AND METHOD FOR REDUCING ADVERSE INTERACTIONS BETWEEN PHENOTHIAZINE DERIVATIVES AND PLASMA USING SURFACTANTS AND AMINO ACIDS

(75) Inventors: Jianwei Yu, Plainsboro, NJ (US); Pui-Ho Yuen, Princeton Junction, NJ (US); Virginia Paulate, Groton, CT (US)

(73) Assignee: Baxter International Inc., Deerfield, IL (US)

( * ) Notice: Subject to any disclaimer, the term of this patent is extended or adjusted under 35 U.S.C. 154(b) by 690 days.

(21) Appl. No.: 10/183,599

(22) Filed: Jun. 26, 2002

(65) Prior Publication Data

US 2003/0032639 A1 Feb. 13, 2003

Related U.S. Application Data

(60) Provisional application No. 60/301,542, filed on Jun. 28, 2001.

(51) Int. Cl.
*A61F 2/02* (2006.01)

(52) U.S. Cl. .................................................. 424/423
(58) Field of Classification Search .................. 424/423
See application file for complete search history.

(56) References Cited

U.S. PATENT DOCUMENTS

| 4,071,620 A | 1/1978 | Sklar |
| 4,246,894 A | 1/1981 | Hamacher |

FOREIGN PATENT DOCUMENTS

| WO | WO 96/11007 | 4/1996 |
| WO | WO 96 11007 A | * 1/2000 |

OTHER PUBLICATIONS

Kuster, J., Increases in Creatine Kinase Activity after Intramuscular Injection of Various Drugs, Med. Welt., vol. 24, 1973, pp. 1328–1330.
"Promethazine Hydrochloride Injection," The United States Pharmacopeia, USP24, Jan. 1, 2000, p. 1412, Rockville, MD, USA.
Kaczmarczyk, Franciszek et al., Chemical Abstracts Database Accession No. 73:7181 (XP–002215218), "Incompatibility in Compound Injections. I. Salting Out," from ACTA Pol. Pharm., 1969, vol. 26(6), pp. 555–558.
Yalkowsky, Samuel H. et al., "In–Vitro Method for Detecting Precipitation of Parenteral Formulations After Injection," Journal of Pharmaceutical Sciences, vol. 72, No. 9, Sep. 1983, pp. 1014–1017.
Med. Welt. 24, 1328–30, J. Kuster (1973).
Phenergan Injection (Wyeth–Ayerst), Physician's Desk Reference, 53 Edition, 1999.
Hager, et al., "Gangrene of the hand following intra–arterial injection," Anest. Analg., 47(4):423–427, 1968.
Webb, et al., "Accidental arterial injection," Am. J. Obstet. Gynecol., 101(3):365–371, 1968.

* cited by examiner

*Primary Examiner*—Carlos A. Azpuru
(74) *Attorney, Agent, or Firm*—Michael C. Mayo; Kenneth E. Jaconetty

(57) ABSTRACT

Compositions and methods are provided for reducing adverse reactions as a result of parenteral administration of certain phenothiazine derivatives such as promethazine, including promethazine hydrochloride. The active compound may be admixed with an effective amount of one or more non-ionic surfactants and at least one amino acid and/or one polyol prior to administration to an animal such as a mammal.

44 Claims, No Drawings

COMPOSITION AND METHOD FOR REDUCING ADVERSE INTERACTIONS BETWEEN PHENOTHIAZINE DERIVATIVES AND PLASMA USING SURFACTANTS AND AMINO ACIDS

This application claims priority from copending provisional application Ser. No. 60/301,542 filed on Jun. 28, 2001.

FIELD OF THE INVENTION

The present invention relates to phenothiazine derivatives, and especially to promethazine hydrochloride. In particular, the invention is directed to new compositions containing promethazine hydrochloride, one or more non-ionic surfactants, and one or more amino acids or polyols. The invention also relates to new methods of minimizing promethazine interactions with plasma proteins. The invention is further directed to the use of amino acids or polyols, together with certain non-ionic surfactants, in formulating stable, injectable aqueous solutions of phenothiazine derivatives, such as promethazine hydrochloride, which reduce or eliminate undesirable interactions with blood plasma.

BACKGROUND OF THE INVENTION

Promethazine, including its pharmaceutically acceptable derivative promethazine hydrochloride (10H-Phenothiazine-10-ethanamine, N,N, α-trimethyl-, monohydrochloride, (±)), is derived from a class of compounds known as phenothiazines. Promethazine has been shown to possess antihistaminic, sedative, antimotion-sickness, antiemetic, and anticholinergic effects. An injectable form of the drug has been indicated for the following conditions: 1) amelioration of allergic reactions to blood or plasma; 2) in anaphylaxis as an adjunct to epinephrine and other standard measures after the acute symptoms have been controlled; 3) for other uncomplicated allergic conditions of the immediate type when oral therapy is impossible or contraindicated; 4) active treatment of motion sickness; 5) preoperative, postoperative, and obstetric (during labor) sedation; 6) prevention and control of nausea and vomiting associated with certain types of anesthesia and surgery; 7) as an adjunct to analgesics for the control of postoperative pain; 8) for sedation and relief of apprehension and to produce light sleep from which the patient can be easily aroused; and 9) intravenously in special surgical situations, such as repeated bronchoscopy, ophthalmic surgery, and poor-risk patients, with reduced amounts of meperidine or other narcotic analgesic as an adjunct to anesthesia and analgesia.

U.S. Pat. Nos. 4,246,894; 4,071,620 and 3,981,398 each describe various injectable formulations of promethazine. The parenteral formulation of promethazine hydrochloride, in most cases, is intended for deep intramuscular injection. In occasional use, it can be given through the route of intravenous (i.v.) injection.

When used intravenously, promethazine hydrochloride is generally given in a concentration not greater than about 25 mg/mL and at a rate which generally should not exceed about 25 mg/min. It is preferable to inject the drug through the tubing of an i.v. infusion set that is known to be functioning satisfactorily. However, some incidents of venous thrombosis at the injection site have been encountered.[1] Other clinical case reports involving the use of promethazine HCl have indicated irritation and other serious adverse reactions at the local area of injection, particularly gangrene at the extremity of the injection site.[2,3] Promethazine hydrochloride has also been reported to raise plasma creatine kinase levels after intramuscular injection, which is an indication of muscle irritation.[4]

In laboratory studies, it has been found that precipitates form immediately when promethazine hydrochloride solution is mixed with plasma in vitro. Without being bound by any particular theory, it is believed that this precipitate formation could be related to the venous thrombosis found at the injection site, as well as the cause of other local adverse reactions involving promethazine injection.

It is therefore an object of the present invention to provide new parenteral formulations of phenothiazine derivatives such as promethazine hydrochloride. These new formulations will contain additives that can minimize the potential of generating precipitate upon administration, thereby reducing the possibility of forming thrombosis, as well as reducing other adverse drug reactions at the local area of, and/or at the distal region to the injection site. The invention should also provide new methods for reducing undesirable side effects, e.g. precipitate formation and pain of injection, associated with the use of intramuscularly-administered promethazine derivatives. The formulations should be storage stable and pharmaceutically acceptable.

SUMMARY OF THE INVENTION

In one embodiment the invention provides a composition suitable for parenteral administration containing one or more phenothiazine derivatives. The composition also includes a pharmaceutically acceptable quantity of at least one non-ionic surfactant and at least one amino acid which are effective in reducing plasma interactions with the phenothiazine derivatives upon administration to a mammal.

Also provided as part of the invention is a pharmaceutical composition suitable for parenteral administration which comprises on a weight/volume (w/v) basis from about 0.1 to about 70% of at least one member selected from the group consisting of promethazine derivatives; from about 0.1 to about 2% of at least one non-ionic surfactant member selected from the group consisting of the partial esters of sorbitol and the polyoxyethylene oxides of long chain fatty acids known as polysorbates, alkylpolyethoxyethanols and alkarylpolyethoxyethanols; and from about 0.1 to about 25% of at least one amino acid.

In a further embodiment of the invention, there is a pharmaceutical composition suitable for parenteral administration which comprises on a weight/volume (w/v) basis from about 0.1 to about 70% of at least one member selected from the group consisting of promethazine derivatives; from about 0.1 to about 10% of at least one non-ionic surfactant member selected from the group consisting of the partial esters of sorbitol and the polyoxyethylene oxides of long chain fatty acids known as polysorbates, alkylpolyethoxyethanols and alkarylpolyethoxyethanols; and from about 10 to about 80% of at least one cosolvent such as a polyol.

The invention is also directed to a method for reducing the formation of precipitates during parenteral administration of promethazine to a mammal, which comprises administering a solution of promethazine together with an effective anti-precipitating quantity of at least one non-ionic surfactant and at least one amino acid.

The invention also provides a method for reducing the incidence of undesirable side effects upon intramuscular or intravenous injection of promethazine to a mammal, which comprises administering a solution of said promethazine together with an effective amount of at least one non-ionic surfactant and at least one polyol.

In still another embodiment, the invention comprises an aqueous injectable solution, which includes promethazine hydrochloride and an effective plasma precipitate-inhibiting quantity of one or more amino acids and at least one non-ionic surfactant selected from the group consisting of polysorbates. The total molar concentration of amino acid(s) in the solution is within the range of about 0.075 M to about 0.45 M. The amino acids may be selected from the group consisting of phenylalanine, methionine, hydroxyproline, proline, cystine, histidine, isoleucine, aspartic acid, glutamic acid, tyrosine and tryptophan, including the pharmaceutically acceptable derivatives and salts thereof.

In addition to the foregoing, there is also provided an aqueous injectable solution of promethazine hydrochloride and an effective plasma precipitate-inhibiting quantity of at least one non-ionic surfactant selected from the group consisting of polysorbates in an amount within the range of about 5% to about 10% by weight of said solution. Also included in the solution is from about 10% to about 30% of at least one member selected from the group consisting of the alkylene glycols and the polyalkylene glycols.

The invention is also directed to a pharmaceutical composition suitable for intravenous or intramuscular administration, comprising on a weight/volume (w/v) basis: from about 1 to about 15% of promethazine hydrochloride; from about 1 to about 10% of at least one amino acid selected from the group consisting of phenylalanine, methionine, hydroxyproline, proline, cystine, histidine, isoleucine, aspartic acid, glutamic acid, tyrosine and tryptophan, including the pharmaceutically acceptable derivatives and salts thereof; from about 0.1 to about 2% of at least one non-ionic surfactant selected from the group consisting of polysorbates; and a pH modifier.

In another aspect, the invention is directed to a pharmaceutical composition suitable for intravenous or intramuscular administration, comprising on a weight/volume (w/v) basis: from about 1 to about 15% of promethazine hydrochloride; from about 5 to about 10% of at least one non-ionic surfactant selected from the group consisting of polysorbates; from about 30% to about 70% of propylene glycol; and a pH modifier.

The invention also includes an aqueous, injectable solution, comprising from about 1 to about 15% of promethazine hydrochloride; from about 1 to about 10% of at least two amino acids selected from the group consisting of phenylalanine, aspartic acid monosodium, L-tryptophan, L-proline, and L-hydroxyproline; from about 0.1 to about 2% of one or more polysorbates; and water.

In addition, the invention also includes an aqueous, injectable solution, comprising: from about 1 to about 15% of promethazine hydrochloride; from about 5 to about 10% of polysorbate 80; from about 30 to about 70% of propylene glycol; and water.

The foregoing and other features and advantages of the invention will become more apparent from the detailed description of the preferred embodiments of the invention given below.

DETAILED DESCRIPTION OF THE PREFERRED EMBODIMENTS

The invention is directed to novel compositions and methods of treatment using phenothiazine derivatives such as promethazine. In particular, the invention is directed to preventing, or at least reducing or minimizing, the undesirable side effects associated with injectable treatments of such promethazine derivatives as promethazine hydrochloride, for example. The compositions and methods hereinafter described should serve to reduce the interaction of promethazine with plasma proteins, thereby reducing the formation of undesirable precipitates. In turn, incidences of such adverse reactions as irritation and venous thrombosis at the site of parenteral administration should be diminished or eliminated.

Phenothiazine is a widely used anthelmintic (worming agent) in veterinary medicine. It is an organic compound which is highly effective against a broad range of parasites in cattle, horses, poultry, sheep, and swine. A highly toxic drug, it is currently not recommended for human use. Derivatives of phenothiazine are, however, now widely prescribed for humans to control mental disorders such as schizophrenia, paranoia, mania, psychosis resulting from mental deficiency, some forms of senility, hyperactivity in children, and even severe anxiety. The most widely used phenothiazine, chlorpromazine (THORAZINE®) is prescribed for overactive schizophrenics. Another compound, trifluoperazine (STELAZINE®) is used for inhibited and withdrawn schizophrenics. In addition, promethazine hydrochloride has been prescribed for its antihistaminic, sedative, antimotion-sickness, antiemetic, and anticholinergic effects.

As part of the invention, there is provided a novel composition containing one or more phenothiazine derivatives as active compounds. These would include, without limitation, all FDA-approved compounds such as chlorpromazine, trifluoperazine and promethazine. Of these, promethazine is preferred, especially as promethazine hydrochloride. By way of non-limiting example, promethazine hydrochloride is identified by the chemical structure:

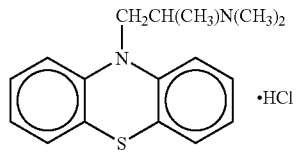

The invention in particular contemplates compositions of phenothiazine derivatives such as promethazine for use in parenteral administration to an animal. The term "parenteral" would therefore encompass all injectables, including without limitation all compositions which are administered intramuscularly, intravenously, intra-arterially, and subcutaneously, for example. The term "animal" would encompass mammals, and in particular would be directed to humans in need of treatment with one or more phenothiazine derivatives such as promethazine and its pharmaceutically acceptable salts and derivatives, such as promethazine hydrochloride.

The compositions herein described may be in any dosage form, but preferably are in liquid form such as in aqueous-based (water) media. Other liquid dosage forms such as emulsions and the like may be contemplated by the skilled artisan provided that they are stable, effective and minimize or eliminate adverse reactions between the active and blood plasma upon administration, as further set forth herein.

A pharmaceutically acceptable quantity of phenothiazine derivative may be utilized, in particular, to yield a dosage amount suitable for an approved indication. As part of the formulation, a preferred concentration will be within the range of about 0.05 to about 95% (w/v) of the phenothiazine derivative(s), e.g. promethazine such as promethazine hydrochloride. Even more preferred is a concentration within the range of about 0.1 to about 70% (w/v), with a range of about 0.1 to about 20% (w/v) being more desirable, and a range of from about 1 to about 15% being even more preferred. The skilled artisan may also utilize promethazine or its derivatives in an amount within a typical dosing range of about 25 milligrams to about 50 milligrams per milliliter of aqueous media.

In addition, the compositions of the invention will contain at least one non-ionic surfactant. Suitable non-ionic surfactants include one or more of the partial esters of sorbitol and the polyoxyethylene oxides of long chain fatty acids known as the polysorbates, the alkylpolyethoxyethanols or alkarylpolyethoxyethanols. Of the foregoing compounds, the polysorbates may be preferred. Polysorbate 80 may be particularly preferred. In one embodiment, the non-ionic surfactant is utilized in an amount less than about 2.0% (w/v). A concentration within the range of about 0.1% to about 2.0% (w/v) is preferred, and a concentration within the range of up to about 1.0% to about 2.0% is more preferred.

Also included in the composition are one or more amino acids. As non-limiting examples, the amino acids can include one or more of the compounds which are selected from the group consisting of phenylalanine, methionine, hydroxyproline, proline, cystine, histidine, isoleucine, aspartic acid, glutamic acid, tyrosine and tryptophan, including the pharmaceutically acceptable derivatives and salts of any of the foregoing. Of these, phenylalanine, aspartic acid monosodium, L-tryptophan, L-proline, and L-hydroxyproline may be preferred. In certain formulations it may be desirable to utilize at least two amino acids, and in some instances, at least three amino acids. The total molar concentration of amino acid(s) in the composition of the invention will typically be within the range of from about 0.075 M to about 0.45 M, with a range of about 0.15 M to about 0.35 M being preferred. Expressed another way, the amino acid(s) may comprise from about 0.1% to about 25% (w/v) of the composition, with a range of about 1 to about 10% being more desirable.

In a further embodiment of the invention, the compositions containing phenothiazine derivatives, such as promethazine and its derivatives, may include a cosolvent to be used with the non-ionic surfactant(s) heretofore described. In these embodiments, the cosolvent will be a polyol, and more preferably a glycol. In particular, the glycol will be selected from the group consisting of alkylene glycols and polyalkylene glycols. Of these, polyethylene glycol (300 and 400) and propylene glycol are preferred. The amount of polyol in the composition will be within the range of from about 10% to about 80% (w/v). More desirably, there will be about 30% to about 70% of polyol utilized, with a range of about 40% to about 60% being more preferred.

When a cosolvent such as a polyol is utilized, the amount of the previously described non-ionic surfactant will typically be larger, and will usually be within the range of about 5% to about 10% (w/v). In addition, the previously described amino acids may or may not be included in the composition when a cosolvent is utilized.

The compositions of the invention according to all their various embodiments may also contain one or more pH modifiers (buffer agents). These are chemical compounds available in the art which are utilized to maintain the composition at a suitable pH. A pH within the range of about 3.5 to about 6.5 is preferred for the composition. Within this range a lower pH is often desirable to help ensure the maximum stability of the preparation. A pH within the range of about 4.3 to about 5.5 is more desirable. Those skilled in the art may discover an optimal pH by analyzing such factors as the heat stability data of the active phenothiazine derivative such as promethazine hydrochloride, in further consideration of the impact of pH on the practical end use of the product.

Other components of the composition of the invention may include one or more anti-oxidants or preservatives to help prevent microbial growth or otherwise inhibit degradation of the final formulation. Any suitable anti-oxidant or preservative stabilizing compound available to the skilled artisan may be utilized in amounts of from about 0.001 to about 1% (w/v) of the composition. For example, sodium metabisulfite or monothioglycerol may be utilized by the skilled artisan as suitable antioxidants and phenol as a proper preservative, for example.

One or more stabilizers may also be utilized in the final formulation. For example, the presence of heavy metal ions is known to accelerate the degradation of an active compound such as promethazine hydrochloride. A chelating agent, such as ethylenediaminetetraacetic acid (EDTA) may therefore be useful in stabilizing the composition. When utilized, the stabilizer(s) are typically present in amounts equal to about 0.001 to about 1% (w/v) of the composition.

Since the formulations herein described are preferably aqueous, water will make up the remainder of the compositions in an amount to bring the total of all constituents to about 100% (w/v). Other types of formulations, e.g. oil-based, emulsion, water-in-oil, etc. may also be utilized, provided that they are storage-stable and effective at delivering the active compound.

The formulations of the invention according to the various embodiments may be prepared by dissolving a suitable quantity of the active phenothiazine derivative, e.g. promethazine such as promethazine hydrochloride, in a liquid medium such as water. One or more excipients as heretofore described are then added, or may already be present in the liquid base. Dosage units for parenteral administration may then be prepared using available techniques. As a non-limiting example, dosage preparations for intravenous delivery of promethazine hydrochloride should typically be administered in a concentration which is less than or equal to about 25 mg/mL or at a rate which is less than or equal to about 25 mg/min. Other concentrations and doses, along with a particular dosing regimen, may then be selected according to the particular indication, typically in consultation with a health professional.

The present invention is further illustrated in more detail by way of the following non-limiting examples.

EXAMPLE 1

An aqueous formulation of promethazine hydrochloride was prepared by dissolving promethazine hydrochloride in a solution of excipients and adjusting the pH with hydrochloric acid/sodium hydroxide (HCl/NaOH). Each mL of the formulation contained 25 mg or 50 mg of promethazine hydrochloride, 15 mg of phenylalanine, 48 mg of aspartic acid monosodium, 10 mg of polysorbate 80, and a certain amount of a chelating agent, such as 0.1 mg of EDTA disodium and an anti-oxidant, such as 0.25 mg of sodium metabisulfite.

EXAMPLE 2

An aqueous formulation of promethazine hydrochloride was prepared by dissolving promethazine hydrochloride in a solution of excipients and adjusting the pH with hydrochloric acid/sodium hydroxide (HCl/NaOH). Each mL of the formulation contained 25 mg or 50 mg of promethazine hydrochloride, 15 mg of phenylalanine, 32 mg of L-tryptophan, 10 mg of polysorbate 80, and a certain amount of a chelating agent, such as 0.1 mg of EDTA disodium and an anti-oxidant, such as 0.25 mg of sodium metabisulfite.

EXAMPLE 3

An aqueous formulation of promethazine hydrochloride was prepared by dissolving promethazine hydrochloride in a solution of excipients and adjusting the pH with hydrochloric acid/sodium hydroxide (HCl/NaOH). Each mL of the formulation contained 25 mg or 50 mg of promethazine hydrochloride, 15 mg of L-proline, 15 mg of L-hydroxyproline, 48 mg of aspartic acid monosodium, 10 mg of polysorbate 80, and a certain amount of a chelating agent, such as 0.1 mg of EDTA disodium and an anti-oxidant, such as 0.25 mg of sodium metabisulfite.

EXAMPLE 4

An aqueous formulation of promethazine hydrochloride was prepared by dissolving promethazine hydrochloride in a solution of excipients and adjusting the pH with hydrochloric acid/sodium hydroxide (HCl/NaOH). Each mL of the formulation contained 25 mg or 50 mg of promethazine hydrochloride, 15 mg of phenylalanine, 15 mg of L-proline, 15 mg of L-hydroxyproline, 10 mg of polysorbate 80, and a certain amount of a chelating agent, such as 0.1 mg of EDTA disodium and an anti-oxidant, such as 0.25 mg of sodium metabisulfite.

EXAMPLE 5

An aqueous formulation of promethazine hydrochloride was prepared by dissolving promethazine hydrochloride in a solution of excipients and adjusting the pH with hydrochloric acid/sodium hydroxide (HCl/NaOH). Each mL of the formulation contained 25 mg or 50 mg of promethazine hydrochloride, 500 mg of propylene glycol, 100 mg of polysorbate 80, and a certain amount of a chelating agent, such as 0.1 mg of EDTA disodium and an anti-oxidant, such as 0.25 mg of sodium metabisulfite.

EXAMPLE 6

An aqueous formulation of promethazine hydrochloride was prepared by dissolving promethazine hydrochloride in a solution of excipients and adjusting the pH with hydrochloric acid/sodium hydroxide (HCl/NaOH). Each mL of the formulation contained 25 mg or 50 mg of promethazine hydrochloride, 500 mg of propylene glycol, 50 mg of polysorbate 80, and a certain amount of a chelating agent, such as 0.1 mg of EDTA disodium and an anti-oxidant, such as 0.25 mg of sodium metabisulfite.

The overall testing results when the formulations from the above examples were mixed with plasma are summarized in Tables 1 and 2. These results showed minimum formation of precipitate when promethazine hydrochloride solution was mixed with plasma in vitro when a combination of non-ionic surfactant and amino acids, or a combination of non-ionic surfactant and cosolvent, was included in the promethazine hydrochloride solution. With a composition according to one or more of the embodiments set forth herein, it is expected that a promethazine solution given by the routes of i.v. and i.m. (intramuscular) injection would have fewer incidences of irritation and other adverse reactions at the site of injection.

TABLE 1

Relative Amount of Precipitate Formed When 1 Part of Promethazine Hydrochloride Preparation is Mixed with 10 Parts of Plasma

| Formulations | Upon Addition to Plasma |
| --- | --- |
| Formulation without non-ionic surfactant and amino acid combination | Large Quantity of Precipitate Forms Immediately |
| Formulation with non-ionic surfactant and amino acid combination | No Precipitate Forms Immediately; Small Amount of Precipitate Forms Over Time |
| Formulation with a non-ionic surfactant and a cosolvent | No Precipitate Forms Within Half Hour |

TABLE 2

Relative Amount of Precipitate Formed When 10 Parts of Promethazine Hydrochloride Preparation is Mixed with 1 Part of Plasma

| Formulations | Upon Addition to Plasma |
| --- | --- |
| Formulation without non-ionic surfactant and amino acid combination | Precipitate Forms Immediately, Redissolves upon Mixing, and Slowly Forms Again over Time |
| Formulation with non-ionic surfactant and amino acid combination | No Precipitate Forms Within Half Hour |
| Formulation with a non-ionic surfactant and a cosolvent | No Immediate Precipitation; Very Small Amount of Precipitate Forms when Mixed |

Although the invention has been described with reference to particular embodiments thereof, it should be appreciated that many changes and modification can be made without departing from the spirit or scope of the invention. Accordingly, the invention is not to be considered as limited by the foregoing description, but is only limited by the scope of the appended claims as they may be ultimately construed.

BIBLIOGRAPHY

1. PHENERGAN® Injection (Wyeth-Ayerst), Physician's Desk Reference, 55thed., 2001.
2. "Gangrene of the Hand Following Intra-Arterial Injection", Hager D L, Wilson, J N: Anesth. Analg., 47(4): 432–427, 1968.
3. "Accidental Arterial Injection", Webb G A, Lampert, N: Am. J. Obstet. Gynecol., 101(3): 365–371, 1968.
4. "Rise of Activity of Creatine Kinase after Intramuscular Injection of Various Drugs", Kuster J, Medizinische Welt 24/35: (1328–1330), 1973.

What is claimed is:

1. A pharmaceutical composition suitable for parenteral administration, comprising in combination:
    a) one or more phenothiazine derivatives;
    b) at least one non-ionic surfactant; and
    c) at least one amino acid, wherein said combination is effective in reducing plasma interactions with said derivatives in a mammal upon administration thereto.

2. The composition of claim 1, wherein said phenothiazine derivative is promethazine hydrochloride.

3. The composition of claim 1, wherein said amino acid is at least one member selected from the group consisting of phenylalanine, methionine, hydroxyproline, proline, cystine, histidine, isoleucine, aspartic acid, glutamic acid, tyrosine and tryptophan, including the pharmaceutically acceptable derivatives and salts thereof.

4. The composition of claim 3, wherein said composition comprises at least two amino acids.

5. The composition of claim 4, wherein said amino acids are selected from the group consisting of phenylalanine, aspartic acid monosodium, L-tryptophan, L-proline, and L-hydroxyproline.

6. The composition of claim 3, wherein said amino acids have a total molar concentration in said composition within the range of about 0.075 M to about 0.45M.

7. The composition of claim 6, wherein said total molar concentration is within the range of about 0.15 M to about 0.35 M.

8. The composition of claim 6, further comprising at least one chelating agent.

9. The composition of claim 8, further comprising at least one antioxidant.

10. The composition of claim 1, wherein said surfactant is at least one member selected from the partial esters of sorbitol and the polyoxyethylene oxides of long chain fatty acids selected from the group consisting of polysorbates, alkylpolyethoxyethanols and alkarylpolyethoxyethanols.

11. The composition of claim 10, wherein said surfactant is polysorbate 80.

12. The composition of claim 9, wherein said surfactant is present in said composition in an amount of from about 0.1% to about 2% (w/v) thereof.

13. The composition of claim 12, wherein said surfactant is present within the range of about 1.0% to about 2.0% (w/v).

14. The composition of claim 1, wherein said composition is administered intramuscularly, intravenously, intra-arterially, or subcutaneously.

15. A pharmaceutical composition suitable for parenteral administration, comprising on a weight/volume (w/v) basis:
   a) from about 0.1 to about 70% of at least one member selected from the group consisting of promethazine derivatives;
   b) from about 0.1 to about 2% of at least one non-ionic surfactant member selected from the partial esters of sorbitol and the polyoxyethylene oxides of long chain fatty acids selected from the group consisting of polysorbates, alkylpolyethoxyethanols and alkarylpolyethoxyethanols; and
   c) from about 0.1 to about 25% of at least one amino acid.

16. The composition of claim 15, wherein said promethazine derivative is promethazine hydrochloride.

17. The composition of claim 15, wherein said amino acid is at least one member selected from the group consisting of phenylalanine, methionine, hydroxyproline, proline, cystine, histidine, isoleucine, aspartic acid, glutamic acid, tyrosine and tryptophan, including the pharmaceutically acceptable derivatives and salts thereof.

18. The composition of claim 16, wherein said non-ionic surfactant is at least one member selected from the group consisting of polysorbates.

19. The composition of claim 18, wherein said nonionic surfactant is polysorbate 80.

20. The composition of claim 17, wherein said composition comprises at least two amino acids.

21. The composition of claim 19, wherein said amino acids are selected from the group consisting of phenylalanine, aspartic acid monosodium, L-tryptophan, L-proline, and L-hydroxyproline.

22. The composition of claim 20 wherein said amino acids are present in an amount within the range of about 1% to about 10% (w/v) of said composition.

23. The composition of claim 21, further comprising a pH modifying agent to maintain said composition within a pH range of about 3.5 to about 6.5.

24. The composition of claim 22, wherein said pH modifying agent is present to maintain said composition within a pH range of about 4.0 to about 5.5.

25. The composition of claim 21, further comprising at least one anti-oxidant.

26. The composition of claim 21, further comprising at least one chelating agent.

27. The composition of claim 26, wherein said chelating agent is ethylenediaminetetraacidic acid (EDTA).

28. The composition of claim 15, wherein said composition is effective in reducing the interaction of plasma proteins with said promethazine derivative upon intramuscular or intravenous administration to an animal.

29. A pharmaceutical composition suitable for parenteral administration, comprising on a weight/volume (w/v) basis:
   a) from about 0.1 to about 70% of at least one member selected from the group consisting of promethazine derivatives;
   b) from about 0.1 to about 10% of at least one non-ionic surfactant member selected from the group consisting of the partial esters of sorbitol and the polyoxyethylene oxides of long chain fatty acids known as polysorbates, alkylpolyethoxyethanols and alkarylpolyethoxyethanols; and
   c) from about 10 to about 80% of at least cosolvent selected from the group consisting of polyols.

30. The composition of claim 29, wherein said polyol is at least one member selected from the group consisting of the alkylene glycols and polyalkylene glycols.

31. The composition of claim 30, wherein said polyol comprises at least one member from the group of propylene glycol and polyethylene glycol.

32. The composition of claim 31, wherein said polyol is propylene glycol.

33. The composition of claim 31 wherein said polyol is present in an amount of from about 40% a to about 60% of said composition.

34. The composition of claim 30, wherein said non-ionic surfactant is polysorbate 80 and is present in an amount of from about 5 to about 10% of said composition.

35. A method for reducing the formation of precipitates during parenteral administration of promethazine to a mammal, which comprises administering a *solution of said promethazine together with an effective anti-precipitating quantity of at least one non-ionic surfactant and at least one amino acid.

36. The method of claim 35, wherein said amino acid is at least one member selected from the group consisting of phenylalanine, methionine, hydroxyproline, proline, cystine, histidine, isoleucine, aspartic acid, glutamic acid, tyrosine and tryptophan, including the pharmaceutically acceptable derivatives and salts thereof.

37. The method of claim 36, wherein said method comprises administering at least two amino acids to said mammal.

38. The method of claim 37, wherein said amino acids are selected from the group consisting of phenylalanine, aspartic acid monosodium, L-tryptophan, L-proline, and L-hydroxyproline.

39. The method of claim 35, wherein said nonionic surfactant is at least one member selected from the group consisting of polysorbates.

40. The method of claim 39, wherein said nonionic surfactant is polysorbate 80.

41. An aqueous injectable solution, comprising promethazine hydrochloride and an effective plasma precipitate-inhibiting quantity of one or more amino acids and at least one non-ionic surfactant selected from the group consisting of polysorbates, wherein the total molar concentration of said amino acid(s) is within the range of about 0.075 M to about 0.45 M, and further wherein said amino acids are selected from the group consisting of phenylalanine, methionine, hydroxyproline, proline, cystine, histidine, isoleucine, aspartic acid, glutamic acid, tyrosine and tryptophan, including the pharmaceutically acceptable derivatives and salts thereof.

42. A pharmaceutical composition suitable for intravenous or intramuscular administration, comprising on a weight/volume (w/v) basis:
   a) from about 1 to about 15% of promethazine hydrochloride;
   b) from about 1 to about 10% of at least one amino acid selected from the group consisting of phenylalanine, methionine, hydroxyproline, proline, cystine, histidine, isoleucine, aspartic acid, glutamic acid, tyrosine and tryptophan, including the pharmaceutically acceptable derivatives and salts thereof;
   c) from about 0.1 to about 2% of at least one non-ionic surfactant selected from the group consisting of polysorbates; and
   d) a pH modifier.

43. The pharmaceutical composition of claim 42, wherein said at least one non-ionic surfactant is polysorbate 80.

44. An aqueous, injectable solution, comprising:
   a) from about 1 to about 15% of promethazine hydrochloride;
   b) from about 1 to about 10% of at least two amino acids selected from the group consisting of phenylalanine, aspartic acid monosodium, L-tryptophan, L-proline, and L-hydroxyproline;
   c) from about 0.1 to about 2% of one or more polysorbates; and
   d) water.

* * * * *